United States Patent [19]

Meiser et al.

[11] 4,060,623
[45] Nov. 29, 1977

[54] 1,2,4-TRIAZOLE ANTIMYCOTIC COMPOSITIONS AND USE THEREOF

[75] Inventors: Werner Meiser, Wuppertal-Elberfeld; Wolfgang Krämer, Wuppertal-Barmen; Karl Heinz Büchel; Manfred Plempel, both of Wuppertal-Elberfeld, all of Germany

[73] Assignee: Bayer Aktiengesellschaft, Germany

[21] Appl. No.: 646,019

[22] Filed: Jan. 2, 1976

Related U.S. Application Data

[62] Division of Ser. No. 532,191, Dec. 12, 1974, Pat. No. 4,002,763, which is a division of Ser. No. 396,202, Sept. 11, 1973, Pat. No. 3,890,442.

[30] Foreign Application Priority Data

Sept. 26, 1972   Germany ............................ 2247186

[51] Int. Cl.$^2$ ............................................ A61K 31/41
[52] U.S. Cl. .................................................... 424/269
[58] Field of Search ......................................... 426/269

[56] References Cited
U.S. PATENT DOCUMENTS 3,755,349   8/1973   Timmler et al. ..................... 424/273

*Primary Examiner*—Jerome D. Goldberg

*Attorney, Agent, or Firm*—Jacobs & Jacobs

[57] ABSTRACT

Antimycotic compositions are produced which comprise an antimycotically effective amount of a 1,2,4-triazole of the formula:

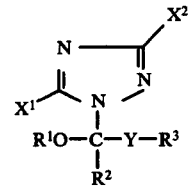

or a pharmaceutically acceptable non-toxic salt thereof wherein
  $X^1$ is hydrogen or alkyl;
  $X^2$ is hydrogen or alkyl;
  $R^1$ is alkyl, unsubstituted or substituted aryl or unsubstituted or substituted aralkyl;
  $R^2$ is hydrogen, alkyl or unsubstituted or substituted aryl;
  $R^3$ is alkyl, cycloalkyl, unsubstituted or substituted aryl or unsubstituted or substituted aralkyl; and
  Y is a keto group or a functional derivative of a keto group, in combination with a pharmaceutically acceptable non-toxic, inert diluent or carrier.

28 Claims, No Drawings

1,2,4-TRIAZOLE ANTIMYCOTIC COMPOSITIONS AND USE THEREOF

This is a division of Ser. No. 532,191 filed Dec. 12, 1974, U.S. Pat. No. 4,002,763, which is a divisional application of U.S. Ser. No. 396,202 filed Sept. 11, 1973, which issued a U.S. Pat. No. 3,890,442 on June 17, 1975.

The present invention relates to antimycotic compositions and to methods of treating mycoses in humans and animals.

More particularly, the present invention relates to pharmaceutical compositions useful for the treatment of mycoses in humans and animals which comprises an antimycotically effective amount of a 1,2,4-triazole as hereinbelow defined, or a pharmaceutically acceptable non-toxic salt thereof in combination with a pharmaceutically acceptable non-toxic inert diluent or carrier, as well as to the treatment of mycoses in humans and animals by administering an antimycotically effective amount of a 1,2,4-triazole as hereinbelow defined.

It has been suggested in the art that 1,2,4-triazoles are effective against fungi pathogenic to plants.

We have now made the surprising discovery that 1,2,4-triazoles of the formula:

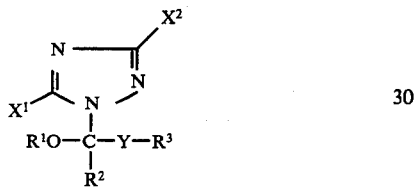

or a pharmaceutically acceptable non-toxic salt thereof wherein $X^1$ is hydrogen or alkyl, preferably of 1 to 3 carbon atoms;

$X^2$ is hydrogen or alkyl, preferably of 1 to 3 carbon atoms;

$R^1$ is alkyl, preferably of 1 to 6 carbon atoms, and especially 1 to 4 carbon atoms, aryl, preferably of 6 to 10 carbon atoms, either unsubstituted or substituted by one or more substituents, preferably one to five substituents or particularly one to three substituents or one or two substituents, which substituents may be the same or different and are selected from the group consisting of alkyl of 1 to 4 carbon atoms, halogen especially fluorine, chlorine or bromine, haloalkyl, preferably of 1 or 2 carbon atoms and of 2 to 5 halogen atoms, especially fluorine and/or chlorine, alkoxy, preferably of 1 or 2 carbon atoms, haloalkoxy, preferably of 1 or 2 carbon atoms and of 2 to 5 halogen atoms, particularly fluorine and/or chlorine, nitro, amino, phenyl, chlorophenyl particularly o-chlorophenyl or p-chlorophenyl, or aralkyl, preferably of 6 to 10 carbon atoms in the aryl portion and 1 or 2 carbon atoms in the alkyl portion either unsubstituted or substituted by one or more substituents, preferably one to five substituents or particularly one to three substituents or one or two substituents, which substituents may be the same or different and are selected from the group consisting of alkyl of 1 to 4 carbon atoms, halogen especially fluorine, chlorine or bromine, haloalkyl, preferably of 1 or 2 carbon atoms and of 2 to 5 halogen atoms, especially fluorine and/or chlorine, alkoxy, preferably of 1 or 2 carbon atoms, haloalkoxy, preferably of 1 or 2 carbon atoms and of 2 to 5 halogen atoms, particularly fluorine and/or chlorine, nitro, phenyl, chlorophenyl particularly o-chlorophenyl or p-chlorophenyl, or amino;

$R^2$ is hydrogen, alkyl, preferably of 1 to 6 carbon atoms, especially of 1 to 4 carbon atoms, or aryl, preferably or 6 to 10 carbon atoms, either unsubstituted or substituted by one or more substituents, preferably 1 to 5 substituents or particularly 1 to 3 substituents or 1 or 2 substituents, which substituents may be the same or different and are selected from the group consisting of alkyl of 1 to 4 carbon atoms, halogen especially fluorine, chlorine or bromine, haloalkyl, preferably of 1 or 2 carbon atoms and of 2 to 5 halogen atoms, especially fluorine and/or chlorine, alkoxy, preferably of 1 or 2 carbon atoms, haloalkoxy, preferably of 1 or 2 carbon atoms and of 2 to 5 halogen atoms, particularly fluorine and/or chlorine, nitro, amino, phenyl, chlorophenyl particularly o-chlorophenyl or p-chlorophenyl, $R^3$ is alkyl, preferably of 1 to 6 carbon atoms, especially of 1 to 4 carbon atoms, cycloalkyl, preferably of 3 to 7 carbon atoms and especially 3, 5 or 6 carbon atoms, aryl, preferably of 6 to 10 carbon atoms, either unsubstituted or substituted by one or more substituents, preferably one to five substituents or particularly one to three substituents or one or two substituents, which substituents may be the same or different and are selected from the group consisting of alkyl of 1 to 4 carbon atoms, halogen especially fluorine, chlorine or bromine, haloalkyl, preferably of 1 or 2 carbon atoms and of 2 to 5 halogen atoms, especially fluorine and/or chlorine, alkoxy, preferably of 1 or 2 carbon atoms, haloalkoxy, preferably of 1 or 2 carbon atoms and of 2 to 5 halogen atoms, particularly fluorine and/or chlorine, nitro, amino, phenyl, chlorophenyl particularly o-chlorophenyl or p-chlorophenyl, or aralkyl preferably of 6 to 10 carbon atoms in the aryl portion and 1 or 2 carbon atoms in the alkyl portion either unsubstituted or substituted by one or more substituents, preferably one to five substituents or particularly one to three substituents or one or two substituents, which substituents may be the same or different and are selected from the group consisting of alkyl of 1 to 4 carbon atoms, halogen especially fluorine, chlorine or bromine, haloalkyl, preferably of 1 or 2 carbon atoms and of 2 to 5 halogen atoms, especially fluorine and/or chlorine, alkoxy, preferably of 1 or 2 carbon atoms, haloalkoxy, preferably of 1 or 2 carbon atoms and of 2 to 5 halogen atoms, particularly fluorine and/or chlorine, nitro, phenyl, chlorophenyl particularly o-chlorophenyl or p-chlorophenyl, or amino; and Y is a keto group or a functional derivative of a keto group, in combination with a pharmaceutically acceptable non-toxic, inert diluent or carrier.

The antimycotic compositions of the present invention show a broad spectrum of activity against fungi pathogenic to humans and animals. The 1,2,4-triazoles and pharmaceutically acceptable non-toxic salts thereof as defined above are useful in treating mycoses in humans and animals by administering an antimycotically effective amount of a 1,2,4-triazole as above defined to said human or animal.

The present invention also includes pharmaceutical compositions in dosage unit form.

Alkyl as used above is intended to include branched alkyl moieties as well as straight chain alkyl moieties.

According to one embodiment of the present invention $X^1$ and $X^2$ are hydrogen or methyl, ethyl, n-propyl or isopropyl, preferably hydrogen or methyl and especially hydrogen.

When $R^1$, $R^2$ and $R^3$ are alkyl moieties, they are preferably methyl, ethyl, n-propyl, i-propyl, n-butyl, i-butyl or t-butyl.

When $R^1$, $R^2$ and $R^3$ are aryl or aralkyl moieties, they are preferably phenyl, naphthyl or benzyl unsubstituted or substituted by preferably 1 to 3 or especially 1 or 2 of the same or different substituents selected from the group consisting of methyl, ethyl, n-propyl, i-propyl, n-butyl, i-butyl, t-butyl, halogen especially fluorine, chlorine or bromine, haloalkyl of 1 or 2 carbon atoms and 2 to 5 halogen atoms, especially fluorine and/or chlorine, and particularly the trifluoromethyl moiety, alkoxy of 1 or 2 carbon atoms, haloalkoxy of 1 or 2 carbon atoms and 2 to 5 halogen atoms particularly fluorine and/or chlorine and particularly fluoromethoxy, difluorochloromethoxy and trifluoroethoxy, nitro, phenyl, o-chlorophenyl, p-chlorophenyl and amino.

When $R^3$ is a cycloalkyl moiety, it is preferably cyclopropyl, cyclopentyl or cyclohexyl.

The preferred functional derivatives of the keto group Y are the keto-hydrate group, acetal groups derived from alkyl alcohols of 1 to 4 carbon atoms, preferably methanol and ethanol, oximes or semicarbazones of the keto group.

According to another embodiment of the present invention, $X^1$ is hydrogen or alkyl of 1 to 3 carbon atoms;
$X^2$ is hydrogen or alkyl of 1 to 3 carbon atoms;
$R^1$ is alkyl of 1 to 6 carbon atoms, aryl of 6 to 10 carbon atoms unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms, and nitro and amino or aryl substituted by phenyl or halophenyl, or aralkyl of 6 to 10 carbon atoms in the aryl moiety and 1 or 2 carbon atoms in the alkyl moiety unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms, nitro and amino or aryl substituted by phenyl and halophenyl;
$R^2$ is hydrogen, alkyl of 1 to 6 carbon atoms or aryl of 6 to 10 carbon atoms unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms, nitro and amino or aryl substituted by phenyl and halophenyl;
$R^3$ is alkyl of 1 to 6 carbon atoms, cycloalkyl of 3 to 7 carbon atoms, aryl of 6 to 10 carbon atoms unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms, nitro and amino or aryl substituted by phenyl and halophenyl or aralkyl of 6 to 10 carbon atoms in the aryl moiety and 1 or 2 carbon atoms in the alkyl moiety unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms nitro and amino or aryl substituted by phenyl and halophenyl; and
Y is CO, $>C=NOH$ or $>C(OH)_2$.

According to another embodiment of the present invention $X^1$ and $X^2$ are each hydrogen;
$R^1$ is phenyl unsubstituted or substituted by 1 to 5 halogeno moieties, by 1 to b 3 members selected from the group consisting of alkyl of 1 to 4 carbon atoms, fluorine, chlorine, bromine, iodine, trifluoromethyl, alkoxy of 1 or 2 carbon atoms and nitro, or by amino, phenyl, chlorophenyl or bromophenyl.
$R^2$ is hydrogen or phenyl;
$R^3$ is alkyl of 1 to 4 carbon atoms, phenyl or chlorophenyl; and
Y is as above defined.

According to another embodiment of the present invention, $X^1$ and $X^2$ are each hydrogen;
$R^1$ is phenyl unsubstituted or substituted by 1 to 3 fluorine, chlorine, bromine, methyl, t-butyl, and trifluoromethyl moieties or by nitro or phenyl;
$R^2$ is hydrogen or phenyl;
$R^3$ is methyl, t-butyl, phenyl or chlorophenyl; and
Y is as above defined.

According to another embodiment of the present invention, $X^1$ and $X^2$ are each hydrogen;
$R^1$ is phenyl, chlorophenyl, dichlorophenyl, trichlorophenyl, tetrachlorophenyl, pentachlorophenyl, fluorophenyl, bromophenyl, chloromethylphenyl, chlorodimethylphenyl, dichlorotrifluoromethylphenyl, chlorobromophenyl, chloronitrophenyl, trifluoromethylphenyl, dichlorotrifluoromethylphenyl, tolyl, dimethylphenyl, t-butylphenyl, methylnitrophenyl, methoxyphenyl, aminophenyl, diphenyl or phenylbromophenyl;
$R^2$ is hydrogen or phenyl;
$R^3$ is methyl, t-butyl, phenyl or chlorophenyl; and
Y is as above defined.

According to a particularly preferred embodiment of the present invention, $X^1$ and $X^2$ are each hydrogen;
$R^1$ is phenyl, unsubstituted or substituted by 1 to 5 and preferably 1 to 3 substituents selected from the group consisting of fluorine, chlorine, bromine, methyl, t-butyl, trifluoromethyl, nitro and phenyl;
$R^2$ is hydrogen or phenyl;
$R^3$ is methyl, t-butyl, phenyl or chlorophenyl; and Y is a keto group, a keto-hydrate group ($>C(OH)_2$), or a keto-oxime group ($>C=NOH$), and hydrochloride salts thereof.

The pharmaceutically acceptable non-toxic salts of the present invention include those formed by the reaction of the 1,2,4-triazoles with a pharmaceutically acceptable non-toxic acid such as the hydrohalic acids, for example, hydrochloric acid and hydrobromic acid especially hydrochloric acid, phosphoric acid, nitric acid, monofunctional and bifunctional carboxylic acids, hydroxy carboxylic acid, for example acetic acid, maleic acid, succinic acid, fumaric acid, tartaric acid, citric acid, salicylic acid, sorbic acid and lactic acid, and 1,5-naphthalenedisulphonic acid. Thus the preferred salts according to the present invention include the hydrochloride, the hydrobromide, the phosphate, the nitrate, monofunctional and bifunctional carboxylates, hydroxycarboxylates, for example, the acetate, maleate, succinate, fumarate, tartrate, citrate, salicylate, sorbate and lactate and 1,5-naphthalenedisulphonate.

The following compounds are representative of those of the present invention:

1-[(2′,4′-dichloro)-phenoxy]-1-[1′,2′,4′-triazolyl-(1′)]-3,3-dimethyl-2-butanone;

1-[4′-chlorophenoxy]-1-[1′,2′,4′-triazolyl-(1′)]-3,3-dimethyl-2-butanone;

ω-[2′,4′-dichloro)-phenoxy]-ω-[1′,2′,4′-triazolyl-(1′)]-aceto-4′-chlorophenone;

1-[4′-fluorophenoxy]-1-[1′,2′,4′-triazolyl-(1′)]-3,3-dimethyl-2-butanone;

1-[p-diphenoxy]-1-[1′,2′,4′-triazolyl-(1′)]-3,3-dimethyl-2-butanone;

1-phenoxy-1-[1′,2′,4′-triazolyl-(1′)]-3,3-dimethyl-2-butanone;

ω-[4′-chlorophenoxy]-ω-phenyl-ω-[1′,2′,4′-triazolyl-(1′)]-acetophenone;

1-[(3′,4′-dimethyl)-phenoxy]-1-[1′,2′,4′-triazolyl-(1′)]-3,3-dimethyl-2-butanone;

1-phenoxy-1-phenyl-1-[1′,2′,4′-triazolyl-(1′)]-3,3-dimethyl-2-butanone hydrochloride and 1-[2′,3′,4′,6′-tetrachloro)-phenoxy]-1-[1′,2′,4′-triazolyl-(1′)]-3,3-dimethyl-2-butanone.

The 1,2,4-triazoles of the present invention can be produced by a number of processes of which four are illustrated below. These processes are designated (a), (b), (c) and (d) for convenience.

According to process (a), a compound of the formula:

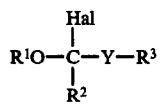

wherein $R^1$, $R^2$, $R^3$ and Y are as above defined and Hal is halogen, especially bromine or chlorine is reacted with a 1,2,4-triazole of the formula:

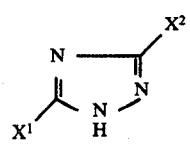

wherein $X^1$ and $X^2$ are as above defined, according to techniques per se known generally in molar amounts either in the presence or in the absence of an acid binding agent such as, for example, triethylamine or an excess of triazole and in the presence of a polar solvent, for example, acetonitrile at a temperature of from about 20° C to about 150° C, preferably at about 80° C to about 120° C. The product is isolated by evaporating the reaction mixture in vacuo and picking up the residue in an organic solvent, for example, methylenechloride. The resulting solution is extracted by shaking with water to remove the triazole halide formed and the organic phase is again distilled in vacuo. The oil which remains after the solvent has passed over is purified either according to techniques per se known via the salt or by recrystallization, for example, from ether.

According to process (b), a compound of the formula:

wherein $R^1$, $R^2$, $R^3$ and Y are as above defined, is reacted with a 1,2,4-triazole of formula III above in a manner per se known, generally in molar amounts either in the presence or in the absence of a dehydrating agent, for example, calcium oxide and either in the presence or in the absence of a high boiling solvent such as chlorobenzene, but preferably in the absence of such a solvent, especially in the melt, at a temperature of from about 100° C to about 230° C, preferably between about 140° C and about 200° C. The resulting products are isolated and purified as described above under process (a).

According to process (c), a compound of the formula IV is reacted with a thionylbistriazole of the formula:

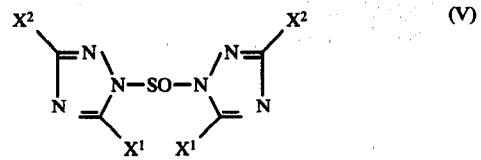

wherein $X^1$ and $X^2$ are as above defined, in equimolar proportions either in the presence or in the absence of a solvent, for example, acetonitrile or benzene at a temperature of from about 20° C to about 100° C. The product is isolated and purified according to procedures per se known and which have been described above under process (a).

According to process (d), a compound of the formula:

wherein $R^1$, $R^2$, $R^3$ and Y are as above defined, is reacted with the hydrochloride of a 1,2,4-triazole of the formula III, generally in approximately molar amounts, either in the presence or in the absence of a diluent such as dioxane or dibutyl ether and in the presence of an acid catalyst, for example, p-toluenesulphonic acid, but preferably in the melt, at a temperature of from about 80° C to about 250° C, preferably between about 120° C and 200° C. The reaction product is isolated and purified as discussed above under process (a).

The salts of the 1,2,4-triazoles of the present invention are produced according to procedures per se known, for example, by dissolving the free base of formula I in ether and adding the appropriate acid.

All starting compounds for the production of the 1,2,4-triazoles of the present invention are either known or obtainable according to known methods.

For example, compounds of formula II can be obtained by reacting an alcohol of the formula:

wherein $R^1$ is as above defined, or the sodium alcoholate of the alcohol with, for example, an approximately molar amount of a compound of the formula:

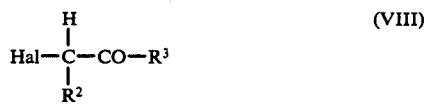

wherein $R^2$, $R^3$ and Hal are as above defined in a manner per se known, for example, in ethyl acetate at the boil. The active hydrogen atom which still remains can subsequently be replaced by halogen according to techniques per se known, for example, by heating with elementary bromine to about 140° C. The keto group can if desired be converted into a functional derivative and the desired product is purified and isolated according to the procedures described above or those which are known.

Compounds of the formula IV which are used as starting materials can be obtained according to procedures per se known from a halogen derivative of the formula II. They can also be produced by procedures per se known, for example, by reacting α,β-diketones or α-ketoaldehydes with alcohols according to the following reaction mechanism:

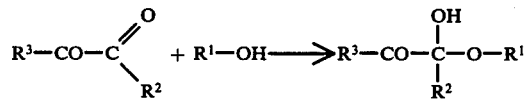

wherein $R^1$, $R^2$ and $R^3$ are as above defined.

If desired, the keto group is converted into a functional derivative according to techniques per se known.

The thionyl-bis-1,2,4-triazoles of the formula V which can be used as starting compounds can be produced according to known processes (compare Angew. Chem. 68, page 754 (1956), for example from the appropriate triazole and thionyl chloride in tetrahydrofuran at room temperature.

The compounds of the formula VI which can be used as starting compounds can be produced by customary methods (compare, for example, J. Chem. Soc. (London) (1970), 3, pages 462 to 464 and Liebigs Ann. Chem. 735 (1970), pages 149, 155, 156, Krohnke, Journal f. praktische Chemie Bd. 11 (1960), 249-255.)

The triazoles of the formula III are either known or obtainable according to procedures per se known.

The 1,2,4-triazoles of the present invention exhibit a broad antimycotic spectrum of activity against annualpathogenic fungi, especially against dermatophytes and blastomycetes as well as against biphase fungi, for example, against species of Candida such as *Candida albicans*, species of Epidermophyton such as *Epidermophyton floccosum*, species of Aspergillus such as *Aspergillus niger*, species of Trichophyton such as *Trichophyton mentagrophytes*, species of Microsporon such as *Microsporon felineum* and species of Penicillium such as *Penicillium commune*.

The 1,2,4-triazoles of the present invention are useful for the treatment of dermatomycoses and systemic mycoses in humans and animals caused by *Trichophyton mentagrophytes* and other species of Trichophyton, species of Microsporon, *Epidermophyton floccosum*, blastomycetes and biphase fungi as well as moulds.

The pharmaceutical compositions of the present invention contain a major or minor amount e.g. 99.5% to 0.1%, preferably 95% to 0.5% of at least one 1,2,4-triazole as above defined in combination with a pharmaceutically acceptable non-toxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 30 to 250, and preferably 50 to 200, mg/kg of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 1.5 to 22.5 g., preferably 2.5 to 18.0 g, of active agent.

While the routes of administration include oral, parenteral (i.e., intramuscular, intraperitoneal, and intravenous), rectal, and topical, oral administration and topical application are particularly preferred.

The preferred pharmaceutical compositions are therefore those in a form suitable for oral administration such as tablets and suspensions and those suitable for topical application such as ointments.

The antimycotic activity of representative compounds according to the present invention is demonstrated from the following in vitro and in vivo experimental data:

1. Determination of the anti-mycotic action spectrum in vitro by the series dilution test.

Description of the experiment

The nutrient substrates used were Sabourauds' milieu d'epreuve for dermatophytes and mould fungi and meat broth-glucose bouillon for blastomyces and biphase fungi. The incubation temperature was 28° C and the incubation time was 24 to 96 hours.

The results of the experiments are summarized in Table A.

Table A

| | Minimum inhibitory concentration in γ/ml of nutrient medium (MIC) | | | | | | | |
|---|---|---|---|---|---|---|---|---|
| Compound from | Trichophyton mentagrophytes | | Candida albicans | | Penicillium | Aspergillus niger | | Microsporon |
| Example No.: | n.s. | w.s. | n.s. | w.s. | commune | n.s. | w.s. | felineum |
| 1 | 4 | 4 | 40 | 40 | >100 | 100 | 100 | 100 |
| 5 | 1* | 32* | >64 | — | >64 | >64 | >64 | >64 |
| 6 | 4* | 10* | 10* | 100* | >100 | 100 | >100 | 40 |
| 9 | 8 | 32 | 100 | >64 | >64 | — | — | — |
| 12 | <1 | <1 | 100* | 100 | 100* | 40* | 100 | 40 |
| 15 | 32 | 32 | >64 | — | >64 | — | — | — |
| 17 | 32 | >64 | 64* | >64 | >64 | — | — | — |
| 21 | 8 | 64 | >64 | >64 | >64 | — | — | — |
| 27 | 4 | 4 | 40 | 100 | >100 | 100 | 100 | — |
| 20 | 32 | >64 | >64 | — | >64 | — | — | — |

Legend:
w.s. = with 30% serum added
n.s. = no serum added
* = 90% inhibition of growth.

2. Antimycotic action of the compounds of the invention, in animal experiments.

a. Topical application in experimental trichophytosis of guinea pigs (pathogen: Trichophyton metagrophytes)

11

Description of the experiment

A 1% strength solution of the active compounds in a dimethylsulphoxide/glycerine/water mixture (1:3:6) or in polyethylene glycol 400 was applied locally for 11 to 14 days after the trichophytosis had been produced experimentally.

The experimental results are shown in Table B.

Table B

| Action of the compounds which can be used according to the invention, in trichophytosis of guinea pigs | |
| --- | --- |
| Compound form Example No. | Action against *Trichophyton mentagrophytes* |
| 12 | ++++ |
| 27 | ++ |

Legend
++ = reduction of symptoms of the infection
+++ = rapid healing of the infection
++++ = complete suppression of symptoms of the infection b. Action, on oral administration, on Quinckeanum trichophytosis of white mice.

It was possible to suppress the development of the Quinckeanum infection in mice with doses of 100 mg/kg of body weight given orally twice daily up to the eighth day of the infection.

The result can be seen from Table C:

Table C

| Action of the compounds of the invention in *Quinckeanum trichophytosis* of white mice | |
| --- | --- |
| Compound from Example No. | Oral action against *Trichophyton mentagrophytes* |
| 12 | ++ |
| 27 | ++++ |

For explanation of symbols, see Table B

For explanation of symbols, see Table B
c. Candidosis of mice.

Description of the experiment

Mice of Type SPF-CF$_1$ were intravenously infected with 1 - 2 × 10$^6$ logarithmically growing Candida cells suspended in physiological sodium chloride solution.

One hour before and 7 hours after infection the animals were treated orally with 2 × 100 mg of the preparations/kg of body weight.

Untreated animals died of the infection 3 to 6 days after infection. The survival rate on the 6th day after infection was about 5% in the case of untreated control animals.

The experimental results are summarized in Table D:

Table D

| Action against Candidosis of mice | |
| --- | --- |
| Compound from Example No.: | Action against *Candida albicans* |
| 12 | + |
| 27 | ++++ |
| 1 | + |
| 6 | + |
| 9 | ++ |

Legend:
+ = 50% survivors on the 6th day after infection
++ = 60-80% survivors on the 6th day after infection
++++ = >80% survivors on the 6th day after infection The following are examples of pharmaceutical compositions according to the invention:
a. 1% strength solution for topical treatment Sufficient polyethylene glycol 400 is added to 1 g of the compound produced in Example 27, while stirring and warming slightly, to give a total of 100 ml of solution.

b. 1% strength ointment for topical treatment 1 g of the compound produced in Example 27 is ground with 5 g of viscous paraffin oil. Thereafter sufficient ointment base of paraffin oil and polyethylene glycol is added to give a total of 100 g of ointment.

c. 10% strength suspension syrup for oral administration.

Sufficient plant oil is added to a mixture of 10 g of the active compound produced in Example 12 and 0.05 g of sodium saccharin and 2 g of colloidal silica and 0.2 g of peppermint oil, to give a total of 100 ml of suspension syrup.

The following is an example of a medicament in dosage unit form according to the invention:

d. Tablet containing 200 mg of active compound, for oral administration 2 g of the compound produced in Example 12, 1 g of lactose and 0.3 g of corn starch are granulated with 0.1 g of corn starch gluten. The mixture is forced through a sieve of about 4 to 6 mm mesh width and is dried. This dried mixture is homogenized through a sieve of 0.8 to 1 mm mesh width and is then mixed with 0.15 g of starch and 0.02 g of magnesium stearate. The mixture thus obtained is pressed to give 10 tablets.

The remaining 1,2,4-triazoles according to the present invention may be formed into pharmaceutical compositions and into compositions in unit dosage form in a similar manner.

The following non-limitative examples more particularly point out and illustrate the present invention:

EXAMPLE 1

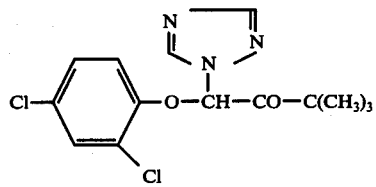

11.2 g (0.033 mol) of 1-bromo-1-2',4'-dichlorophenoxy)-3,3-dimethyl-butan-2-one and 9.9 g (0.15 mol) of 1,2,4-triazole are dissolved in 80 ml of acetonitrile and the solution is heated under reflux for 48 hours. Thereafter the solvent is distilled off in vacuo, the residue is taken up in 150 ml of water and the aqueous solution is extracted by shaking three times with 40 ml of methylene chloride at a time. The organic phase is thereafter twice washed with 150 ml of water at a time, dried over sodium sulphate and distilled.

The oil obtained as a residue is fractionally recrystallised from a little ether, whereby first 1 g of a product of melting point 145° C, which, being a by-product, was not identified, is obtained, followed by 7.6 g (70% of theory) of 1-[2',4'-dichloro-)-phenoxy]-1-[1',2',4'-triazolyl-(1')]-3,3-dimethyl-butan-2-one of melting point 65° C.

The starting compound of the formula

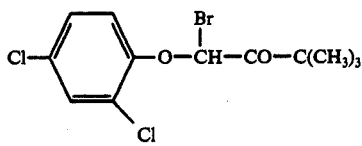

is produced as follows:

35.8 g (0.2 mol) of α-bromo-pinacolone in 50 ml of ethyl acetate are added dropwise to sodium 2,4-dichlorophenolate which is manufactured from 32.6 g (0.2 mol) of 2,4-dichlorophenol and 4.6 g (0.2 mol) of sodium in 130 ml of absolute alcohol, and the mixture is heated to the boil overnight. Thereafter, the sodium bromide produced is filtered off hot, the filtrate is distilled in vacuo and the solid residue is recrystallised from a little ligroin.

38 g (73% of theory) of 1-(2',4'-dichlorophenoxy)-3,3-dimethyl-butan-2-one of melting point 65° C are obtained.

6 ml (0.11 mol) of bromine are added to 26.1 g (0.1 mol) of 1-(2',4'-dichlorophenoxy)-3,3-dimethyl-butan-2-one and the mixture is heated for 1 hour to 140° C under reflux. The resulting oily residue is taken up in petroleum ether, whereupon it crystallises; the solid residue is filtered off and well rinsed.

30 g (89% of theory) of 1-bromo-1-(2',4'-dichlorophenoxy)-3,3-dimethyl-butan-2-one of melting point 70° C are thus obtained.

The remaining starting compounds of this type are obtainable in the same manner.

Production of the hydrochloride of the compound from Example 1:

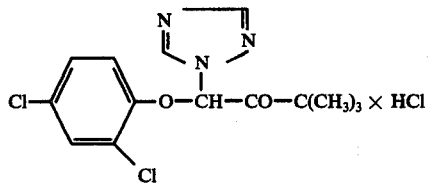

1-[(2',4'-Dichloro)-phenoxy]-1-[1',2',4'-triazolyl-(1)]-3,3-dimethyl-butan-2-one is suspended in anhydrous ether and hydrochloric acid in ether is added. Hereupon, solution gradually occurs. The solvent is distilled off in vacuo. The residue left is recrystallised from isopropanol.

The [1-[(2',4'-dichloro)-phenoxy]-1-[1',2',4'-triazolyl-(1')]-3,3-dimethyl-butan-2-one] hydrochloride thus obtained has a melting point of 125 to 127° C.

EXAMPLE 2

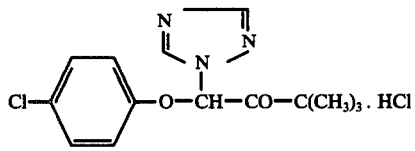

17.7 g (0.05 mol) of 1,1-bis-(4'-chlorophenoxy)-3,3-dimethyl-butan-2-one are intimately mixed with 5.9 g (0.055 mol) of 1,2,4-triazole hydrochloride and the mixture is heated to 220° C over the course of 1 hour and left at this temperature for 30 minutes; in the course thereof, the 4-chlorophenol eliminated boils.

After cooling, 100 ml of 10% strength sodium hydroxide solution are added and this is covered with 200 ml of ether. The ether phase is separated off and washed with three 30 ml portions of 5% strength sodium hydroxide solution and two 50 ml portions of water. After drying over sodium sulphate, the solvent is distilled off in vacuo. The oily residue is taken up in 100 ml of anhydrous ether and 0.055 mol of hydrogen chloride is passed into this solution. This gives a precipitate which after standing overnight is filtered off and rinsed with ether.

7.3 g (46% of theory) of [1-[4'-chlorophenoxy]-1-[1',2',4'-triazolyl-(1')]-3,3-dimethyl-butan-2-one] hydrochloride of melting point 103° to 105° C are obtained.

The starting compound of the formula:

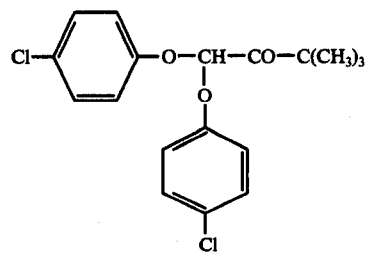

is produced as follows:

6.5 g (0.2 mol) of 80% strength sodium hydride are suspended in 100 ml of anhydrous acetonitrile and 27 g (0.21 mol) of 4-chlorophenol in 50 ml of acetonitrile are added dropwise at room temperature whilst stirring and cooling.

After completion of the evolution of hydrogen, a further 27 g (0.105 mol) of 1,1-dibromo-3,3-dimethyl-butan-2-one (produced in a known manner, for example according to Organic Synthesis, 10, page 12) are added whilst stirring and cooling. Thereafter the mixture is slowly heated to the boil and is boiled for 12 hours under reflux.

After cooling, the solvent is distilled off in vacuo, the residue is boiled up with hot ethyl acetate, active charcoal, is added, the mixture is filtered and is again boiled up briefly and the solution is distilled first in vacuo and, after the solvent has passed over, in a high vacuum.

54 g (76.5% of theory) of 1,1-bis-(4'-chlorophenoxy)-3,3-dimethyl-butan-2-one of boiling point 150° C (0.1 mm Hg) are obtained. The viscous oil solidifies after some time.

The remaining starting compounds of this type can be obtained in the same manner.

EXAMPLE 3

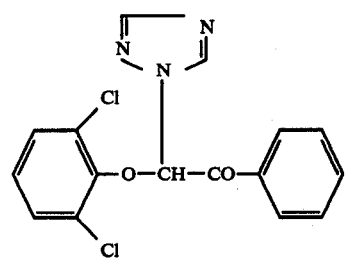

18.0 g (0.05 mol) of ω-bromo-ω-(2',6'-dichlorophenoxy)-acetophenone and 15 g (0.22 mol) of 1,2,4-triazole are dissolved in 120 ml of acetonitrile and heated under reflux for 48 hours. After distilling off the solvent in vacuo, the residue is taken up in 400 ml of water. This aqueous solution is extracted with methylene chloride as described, the organic phase is washed with two 100 ml portions of water and then dried over sodium sulphate, and the solvent is distilled off in vacuo. The resulting oily residue crystallises on heating with ether.

After recrystallisation from ethylene chloride, 7 g (40% of theory) of ω-[(2',6'-dichlorophenoxy)]-ω-[1',2',4'-triazolyl-(1')-]-acetophenone of melting point 130° C are obtained.

The ω-Bromo-ω-(2',6'-dichlorophenoxy)-acetophenone used as the starting material is produced by condensation of 2,6-dichlorophenol with ω-chloroacetophenone and bromination of the resulting ω-(2',6'-dichlorophenoxy)-acetophenone in a customary and known manner, and has a melting point of 58° C.

The remaining starting compounds of this type are obtainable in the same manner.

EXAMPLE 4

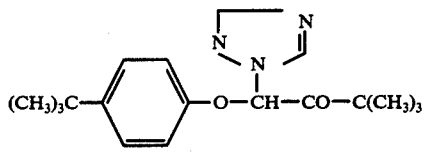

39 g (0.12 mol) of 1-bromo-1-(4'-tert.-butylphenoxy)-3,3-dimethyl-butan-2-one and 24 g (0.35 mol) of 1,2,4-triazole are dissolved in 240 ml of acetonitrile and the solution is heated to the boil under reflux for 24 hours. Thereafter the solvent is distilled in vacuo, ice water is added to the residue and the mixture is extracted with three 40 ml portions of methylene chloride. The organic phase is separated off and washed with two 200 ml portions of water and dried over sodium sulphate, and the solvent is distilled off in vacuo.

The residue is recrystallised from ligroin. 26 g (69% of theory) of 1-[(4'-tert.-butylphenoxy)]-1-[1',2',4'-triazolyl](1')]-3,3-dimethyl-butan-2-one of melting point 115° C are obtained.

1-Bromo-1-[(4'-tert.-butylphenoxy)]-3,3-dimethyl-butan-2-one (melting point 50° C), used as the starting material, is obtained by condensation of p-t-butylphenol with α-bromopinacolone-(2) and subsequent bromination.

The remaining starting compounds of this type are obtainable in the same manner.

EXAMPLE 5

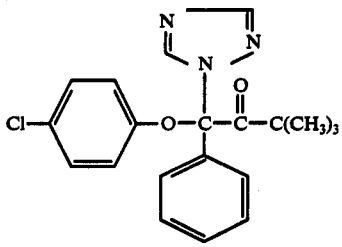

19.0 g (0.05 mol) of 1-bromo-1-(4'-chlorophenoxy)-1-phenyl-3,3-dimethyl-butan-2-one are dissolved in 120 ml of acetonitrile, 12 g (0.175 mol) of 1,2,4-triazole are then added and the solution is heated under reflux for 12 hours. After distilling off the solvent in vacuo, 200 ml of ice water are added. Thereafter the mixture is extracted with four 50 ml portions of methylene chloride and the organic phase is separated off and washed with three 50 ml portions of water. It is dried and the solvent is distilled off in vacuo. The oily residue is recrystallised from ligroin.

5.3 g (29% of theory) of 1-[(4'-chlorophenoxy)]-1-[phenyl]-1-[1',2',4'-triazolyl-(1')]-3,3-dimethyl-butan-2-one of melting point 130° C are obtained.

The starting material of the formula

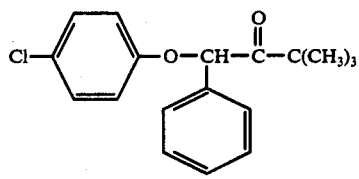

is produced as follows:

The Grignard compound is produced from 38 g of (0.3 mol) of benzyl chloride and 7.3 g (0.3 mol) of magnesium in 300 ml of anhydrous ether. 21 g (0.25 mol) of pivalonitrile in 100 ml of anhydrous ether are added dropwise thereto at the boil and the mixture is kept boiling under reflux for 3 hours.

After cooling, the reaction mixture is introduced into 1.5 liters of ice water, the ether phase is separated off and discarded and the aqueous phase is stirred for 2 hours on a water bath. In the course thereof, the mixture gradually assumes an oily consistency. The oil is repeatedly extracted with 250 ml of methylene chloride and the organic phase is washed with water, dried and subjected to vacuum distillation.

40.5 g (92% of theory) of 1-phenyl-3,3-dimethyl-butan-2-one of boiling point (18 mm Hg) 86° to 88° C are obtained.

17.6 g (0.1 mol) of 1-phenyl-3,3-dimethyl-butan-2-one are dissolved in 100 ml of carbon tetrachloride, 5 ml (0.1 mol) of bromine are added dropwise thereto whilst stirring and under reflux, and the mixture is heated to the boil for one hour. After cooling, and distilling off the solvent, 25.4 g of 1-bromo-1-phenyl-3,3-dimethyl-butan-2-one of melting point 38° to 42° C are obtained in quantitative yield.

A solution of 25.4 g (0.1 mol) of 1-bromo-1-phenyl-3,3-dimethyl-butan-2-one in 50 ml of ethyl acetate is added dropwise, at the boil, to a solution of 12.85 g (0.1 mol) of 4-chlorophenol and 2.3 g (0.1 mol) of sodium in 100 ml of ethanol. After boiling for 12 hours under reflux, the sodium bromide which has separated out is filtered off hot. The filtrate is distilled in vacuo and the solid residue which remains is recrystallised from ligroin. 20.2 g (67% of theory) of 1-[(4'-chlorophenoxy)]-1-[phenyl]-3,3-dimethyl-butan-2-one of melting point 103° C are obtained.

Other starting materials of this type are obtainable in an analogous manner.

The compounds set forth in Table 1 are produced according to an analogous procedure from that described in Examples 1 to 5.

Table 1

Structure:
$X^1$ and $X^2$ substituted triazole with $R^1-O-C(R^2)-Y-R^3$

| Example No. | $R^1$ | $R^2$ | $R^3$ | Y | $X^1$ | $X^2$ | Melting Point °C |
|---|---|---|---|---|---|---|---|
| 6 | 2,4-dichlorophenyl | H | 4-chlorophenyl | CO | H | H | 101–104 |
| 7 | 2,6-dichlorophenyl | H | $C(CH_3)_3$ | CO | H | H | 186 |
| 8 | 4-bromophenyl | H | $C(CH_3)_3$ | CO | H | H | 89–92 |
| 9 | 4-fluorophenyl | H | $C(CH_3)_3$ | CO | H | H | Boiling point 0.3 mm/160 °C |
| 10 | 4-chloro-2-methylphenyl | H | $C(CH_3)_3$ | CO | H | H | 94–96 |
| 11 | 4-nitrophenyl | H | $C(CH_3)_3$ | CO | H | H | 145 |
| 12 | 4-biphenyl | H | $C(CH_3)_3$ | CO | H | H | 105–106 |
| 13 | diphenylmethyl | H | $C(CH_3)_3$ | CO | H | H | 70–73 |
| 14 | 2,4-dichlorophenyl | H | $CH_3$ | CO | H | H | Hydrochloride 125–131 |
| 15 | phenyl | H | $C(CH_3)_3$ | CO | H | H | 62 |
| 16 | 2,6-dimethylphenyl | H | $C(CH_3)_3$ | CO | H | H | Boiling point 151 °C/0.1 mm |

Table 1-continued $$\underset{R^2}{\overset{X^1}{\underset{R^1-O-C-Y-R^3}{\diagdown}}}\overset{N-N}{\underset{N}{\diagdown}}\overset{X^2}{\diagup}$$

| Example No. | R¹ | R² | R³ | Y | X¹ | X² | Melting Point ° C |
|---|---|---|---|---|---|---|---|
| 17 | 2,4-dimethylphenyl (H₃C, H₃C) | H | C(CH₃)₃ | CO | H | H | 71 |
| 18 | 2,5-dichlorophenyl (Cl, Cl) | H | C(CH₃)₃ | CO | H | H | 110 |
| 19 | 4-chlorophenyl (Cl) | H | CH₃ | CO | H | H | Hydrochloride 78–81 |
| 20 | 2,4,5-trichlorophenyl (Cl, Cl, Cl) | H | C(CH₃)₃ | CO | H | H | 142–145 |
| 21 | 2,4-dichlorophenyl (Cl, Cl) | phenyl | C(CH₃)₃ | CO | H | H | Hydrochloride 133–138 |
| 22 | 2-chloro-4-methylphenyl (H₃C, Cl) | H | C(CH₃)₃ | CO | H | H | 88–89 |
| 23 | 2-chloro-3,5-dimethylphenyl (H₃C, Cl, H₃C) | H | C(CH₃)₃ | CO | H | H | 101 |
| 24 | F₃C-, Cl₂- substituted phenyl * | H | C(CH₃)₃ | CO | H | H | 135–138 |
| 25 | 3-trifluoromethylphenyl (F₃C) | H | C(CH₃)₃ | CO | H | H | 74–75 |
| 26 | 4-nitrophenyl (O₂N) | H | C(CH₃)₃ | C=NOH | H | H | 187 |
| 27 | 4-chlorophenyl (Cl) | H | C(CH₃)₃ | CO | H | H | 75 |

Table 1-continued $$\underset{R^1-O-\underset{R^2}{\overset{|}{C}}-Y-R^3}{X^1\diagdown\underset{N}{\overset{N}{\diagdown}}\diagup\overset{N}{\diagdown}\diagup X^2}$$

| Example No. | R[1] | R[2] | R[3] | Y | X[1] | X[2] | Melting Point °C |
|---|---|---|---|---|---|---|---|
| 28 | 4-Cl-C₆H₄- | H | C(CH₃)₃ | C=NOH | H | H | 194–205 |
| 29 | 2,4-Cl₂-5-CH₃-C₆H₂- | H | C(CH₃)₃ | CO | H | H | 114 |
| 30 | C₆Cl₅- | H | C(CH₃)₃ | C(OH)₂ | H | H | 206–207 |
| 31 | C₆H₅- | H | C₆H₅- | CO | H | H | 65–70 |
| 32 | 2,3-Cl₂-C₆H₃- | H | C₆H₅- | CO | H | H | Hydrochloride 126 |
| 33 | 4-H₂N-C₆H₄- | H | C(CH₃)₃ | CO | H | H | 122–125 |
| 34 | 2-Cl-C₆H₄- | H | C(CH₃)₃ | CO | H | H | 68–69 |
| 35 | 3-Cl-C₆H₄- | H | C(CH₃)₃ | CO | H | H | 65–67 |
| 36 | 3,4-Cl₂-C₆H₃- | H | C(CH₃)₃ | CO | H | H | 82–84 |
| 37 | 3-Cl-4-Br-C₆H₃- | H | C(CH₃)₃ | CO | H | H | 94–96 |
| 38 | 4-CH₃-C₆H₄- | H | C(CH₃)₃ | CO | H | H | 74–76 |

Table 1-continued $$\begin{array}{c} X^1-C{=}N{-}N{=}C-X^2 \\ \phantom{X^1-}N\phantom{=N-N=C-X^2} \\ R^1-O-C-Y-R^3 \\ \phantom{R^1-O-}R^2 \end{array}$$

| Example No. | R¹ | R² | R³ | Y | X¹ | X² | Melting Point ° C |
|---|---|---|---|---|---|---|---|
| 39 | 2-methoxyphenyl | H | C(CH₃)₃ | CO | H | H | 87 |
| 40 | 2,4-dimethylphenyl | H | C(CH₃)₃ | CO | H | H | 74 |
| 41 | 4-methyl-3-nitrophenyl | H | C(CH₃)₃ | CO | H | H | 154 |
| 42 | 3-chloro-4-nitrophenyl | H | C(CH₃)₃ | CO | H | H | 100–104 |
| 43 | 3-bromo-4-biphenylyl | H | C(CH₃)₃ | CO | H | H | 125 |
| 44 | 4-chlorophenyl | H | C(CH₃)₃ | CO | H | H | Sulphate 141 |
| 45 | 4-chlorophenyl | H | C(CH₃)₃ | CO | H | H | Nitrate 140, decomposition |
| 46 | 4-chlorophenyl | H | C(CH₃)₃ | CO | H | H | 1,5-Naphthalene-disulphonate 270–273, decomposition |
| 47 | 4-nitrophenyl | H | C(CH₃)₃ | CO | H | H | Hydrochloride 126–130 |
| 48 | 4-nitrophenyl | H | C(CH₃)₃ | CO | H | H | Sulphate 169–171 |
| 49 | 4-nitrophenyl | H | C(CH₃)₃ | CO | H | H | Nitrate 140–141, decomposition |
| 50 | 4-nitrophenyl | H | C(CH₃)₃ | CO | H | H | 1,5-Naphthalene-disulphonate 255, decomposition |

Table 1-continued $$R^1-O-\underset{\underset{R^2}{|}}{\overset{\overset{\displaystyle X^1\diagdown_N\diagup^{N-\diagdown}\diagup^{X^2}}{|}}{C}}-Y-R^3$$

| Example No. | R¹ | R² | R³ | Y | X¹ | X² | Melting Point °C |
|---|---|---|---|---|---|---|---|
| 51 | 2,4-dichlorophenyl (Cl at positions on ring) | H | C(CH₃)₃ | CO | H | H | Sulphate 145–148 |
| 52 | trichlorophenyl | H | C(CH₃)₃ | CO | H | H | Nitrate 133, decomposition |
| 53 | dichlorophenyl | H | C(CH₃)₃ | CO | H | H | 1,5-Naphthalene-disulphonate 250, decomposition |

*The exact position of the chlorine atoms is not known

What is claimed is:

1. An antimycotic composition for treating mycotic infections in humans and animals which comprises an antimycotically effective amount of a 1,2,4-triazole of the formula:

$$R^1O-\underset{\underset{R^2}{|}}{\overset{\overset{\displaystyle X^1\diagdown_N\diagup^{N-\diagdown}\diagup^{X^2}}{|}}{C}}-Y-R^3$$

wherein
X¹ is hydrogen or alkyl of 1 to 3 carbon atoms;
X² is hydrogen or alkyl of 1 to 3 carbon atoms;
R¹ is phenyl unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms, and nitro, or by one substituent selected from the group consisting of phenyl, halophenyl or amino;
R² is hydrogen or alkyl of 1 to 6 carbon atoms;
R³ is phenyl unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms, and nitro, or by one substituent selected from the group consisting of phenyl, halophenyl or amino; and
Y is CO;
in combination with a pharmaceutically acceptable non-toxic, inert carrier.

2. A composition according to claim 1 wherein
X¹ and X² are each hydrogen;
R¹ is phenyl unsubstituted or substituted by 1 to 5 halogeno moieties, by 1 to 3 substituents selected from the group consisting of alkyl of 1 to 4 carbon atoms, fluorine, chlorine, bromine, iodine, trifluoromethyl, alkoxy of 1 or 2 carbon atoms and nitro or by amino, phenyl, chlorophenyl or bromophenyl;
R² is hydrogen; and
R³ is phenyl or chlorophenyl.

3. A composition according to claim 1 wherein
R¹ is phenyl unsubstituted or substituted by 1 to 3 substituents selected from the group consisting of fluorine, chlorine, bromine, methyl, t-butyl and trifluoromethyl, or by nitro or phenyl; and
R³ is phenyl or chlorophenyl.

4. A composition according to claim 1 wherein
R¹ is phenyl, chlorophenyl, dichlorophenyl, trichlorophenyl, tetrachlorophenyl, pentachlorophenyl, fluorophenyl, bromophenyl, chloromethylphenyl, chlorodimethylphenyl, dichlorotrifluoromethylphenyl, chlorobromophenyl, chloronitrophenyl, trifluoromethylphenyl, dichlorotrifluoromethylphenyl, tolyl, dimethylphenyl, t-butylphenyl, methylnitrophenyl, methoxyphenyl, aminophenyl, diphenyl or phenylbromophenyl; and
R³ is methyl, t-butylphenyl or chlorophenyl.

5. A composition according to claim 1 wherein the 1,2,4-triazole is in the form of a salt and said salt is selected from the group consisting of the hydrohalides, the phosphates, nitrates, monofunctional and difunctional carboxylates, hydroxycarboxylates and 1,5-naphthalenedisulphonate.

6. A composition according to claim 5 wherein the salt is selected from the group consisting of the hydrochloride, the hydrobromide, the phosphate, nitrate, acetate, maleate, succinate, fumarate, tartrate, citrate, salicylate, sorbate, lactate and 1,5-naphthalenedisulphonate.

7. A composition according to claim 1 wherein the 1,2,4-triazole is in the form of the hydrochloride salt.

8. A composition according to claim 1 wherein the 1,2,4-triazole is of the formula:

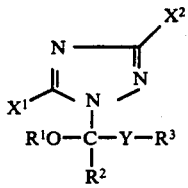

wherein
X$^1$ is hydrogen;
X$^2$ is hydrogen;
R$^1$ is

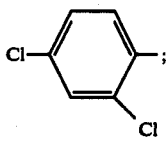

R$^2$ is hydrogen;
R$^3$ is

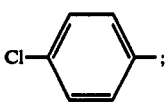

and
Y is CO.

9. A composition according to claim 1 in oral administration form.

10. A composition according to claim 1 in topical application form.

11. A composition according to claim 1 in the form of a tablet.

12. A composition according to claim 11 wherein each tablet contains 200 ml of active agent.

13. A composition according to claim 1 wherein the compound is

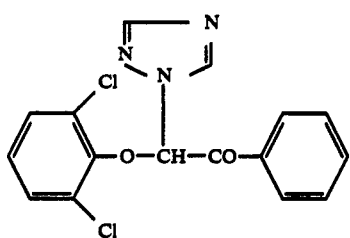

14. A method for treating mycotic infections in humans and animals which comprises administering to a human or animal in need thereof an antimycotically effective amount of a 1,2,4-triazole of the formula:

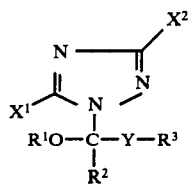

wherein
X$^1$ is hydrogen or alkyl of 1 to 3 carbon atoms;
X$^2$ is hydrogen or alkyl of 1 to 3 carbon atoms;
R$^1$ is phenyl unsubstituted or substituted by one to five substituents selected from the group consisting of alkyl of 1 to 4 carbon atoms, the same or different halogen, the same or different haloalkyl of 1 to 2 carbon atoms and 2 to 5 halogen atoms, alkoxy of 1 or 2 carbon atoms, the same or different haloalkoxy of 1 or 2 atoms and 2 to 5 halogen atoms, and nitro, or by one substituent selected from the group consisting of phenyl, halophenyl or amino;
R$^2$ is hydrogen or alkyl of 1 to 6 carbon atoms;
R$^3$ is phenyl unsubstituted or substituted by one to five substituents selected from the group consisting of alkyl of 1 to 4 carbon atoms, the same or different halogen, the same or different haloalkyl of 1 or 2 carbon atoms and 2 to 5 halogen atoms, alkoxy of 1 or 2 carbon atoms, the same or different haloalkoxy of 1 or 2 carbon atoms and 2 to 5 halogen atoms, alkoxy of 1 or 2 carbon atoms, the same or different haloalkoxy of 1 or 2 carbon atoms and 2 to 5 halogen atoms, and nitro, or by one substitutent selected from the group consisting of phenyl, halophenyl or amino; and
Y is CO;
in combination with a pharmaceutically acceptable non-toxic, inert carrier.

15. A method according to claim 14 wherein
X$^1$ and X$^2$ are each hydrogen;
R$^1$ is phenyl unsubstituted or substituted by 1 to 5 halogeno moieties, by 1 to 3 substituents selected from the group consisting of alkyl of 1 to 4 carbon atoms, fluorine, chlorine, bromine, iodine, trifluoromethyl, alkoxy of 1 or 2 carbon atoms and nitro or by amino, phenyl, chlorophenyl or bromophenyl;
R$^2$ is hydrogen; and
R$^3$ is phenyl or chlorophenyl.

16. A method according to claim 14 wherein
R$^1$ is phenyl unsubstituted or substituted by 1 to 3 substituents selected from the group consisting of fluorine, chlorine, bromine, methyl, t-butyl and trifluoromethyl, or by nitro or phenyl; and
R$^3$ is phenyl or chlorophenyl.

17. A method according to claim 14 wherein
R$^1$ is phenyl, chlorophenyl, dichlorophenyl, trichlorophenyl, tetrachlorophenyl, pentachlorophenyl, fluorophenyl, bromophenyl, chloromethylphenyl, chlorodimethylphenyl, chlorobromophenyl, chloronitrophenyl, trifluoromethylphenyl, dichlorotrifluoromethyl, tolyl, dimethylphenyl, t-butylphenyl, methylnitrophenyl, methoxyphenyl, aminophenyl, diphenyl or phenylbromophenyl; and
R$^3$ is or chlorophenyl.

18. A method according to claim 14 wherein the 1,2,4-triazole is in the form of a salt and said salt is selected from the group consisting of the hydrohalides, the phosphates, nitrates, monofunctional and difunctional carboxylates, hydroxycarboxylates and 1,5-naphthalenedisulphonate.

19. A method according to claim 18 wherein the salt is selected from the group consisting of the hydrochloride, the hydrobromide, the phosphate, nitrate, acetate, maleate succinate, fumarate, tartrate, citrate, salicylate, sorbate, lactate and 1,5-naphthalenedisulphonate.

20. A method according to claim 14 wherein the 1,2,4-triazole is in the form of the hydrochloride salt.

21. The method according to claim 14 wherein the 1,2,4-triazole is of the formula:

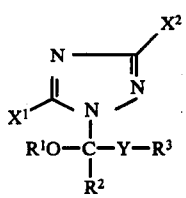

wherein
  $X^1$ is hydrogen;
  $X^2$ is hydrogen;
  $R^1$ is

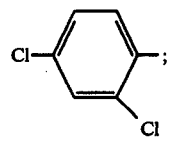

$R^2$ is hydrogen;
  $R^3$ is

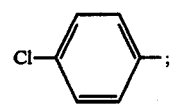

and
  Y is Co.

22. A method according to claim 14 wherein the administration is oral.

23. A method according to claim 14 wherein the administration is by topical application.

24. A method according to claim 14 wherein the administration is by tablet.

25. A method according to claim 24 wherein each tablet contains 200 ml of active agent.

26. A method according to claim 14 wherein the antimycotically effective amount is from 300 to 250 mg/kg per day.

27. A method according to claim 26 wherein the antimycotically effective amount is from 50 to 200 mg/kg. per day.

28. A method according to claim 14 wherein the compound is

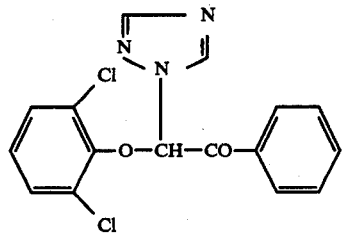

* * * * *